US012458746B2

(12) United States Patent
Cook et al.

(10) Patent No.: US 12,458,746 B2
(45) Date of Patent: Nov. 4, 2025

(54) MEDICAL DEVICE PACKAGING AND RELATED METHODS

(71) Applicant: Regeneron Pharmaceuticals, Inc., Tarrytown, NY (US)

(72) Inventors: Andrew Cook, Troy, NY (US); Victor Bradford, Troy, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 25 days.

(21) Appl. No.: 18/466,173

(22) Filed: Sep. 13, 2023

(65) Prior Publication Data

US 2023/0414859 A1 Dec. 28, 2023

Related U.S. Application Data

(63) Continuation of application No. 17/495,407, filed on Oct. 6, 2021, now Pat. No. 11,793,926, which is a (Continued)

(51) Int. Cl.
*A61M 5/00* (2006.01)
*B65B 69/00* (2006.01)

(52) U.S. Cl.
CPC ............. *A61M 5/002* (2013.01); *B65B 69/00* (2013.01); *B65B 69/005* (2013.01)

(58) Field of Classification Search
CPC ... B65B 69/00; B65B 69/005; B65B 69/0058; A61M 5/002
See application file for complete search history.

(56) References Cited

U.S. PATENT DOCUMENTS 660,782 A 10/1900 Struempell
2,955,705 A 10/1960 Krueger, Sr. et al.
(Continued)

FOREIGN PATENT DOCUMENTS

CA 2280941 A1 6/1999
CN 102482017 A 5/2012
(Continued)

OTHER PUBLICATIONS

International Search Report for PCT/US2020/044058 mailed Nov. 3, 2020.
(Continued)

*Primary Examiner* — Stephen F. Gerrity
(74) *Attorney, Agent, or Firm* — Bookoff McAndrews, PLLC

(57) ABSTRACT

According to one aspect of the disclosure, packaging for a sterile syringe having a nominal size of less than 1 mL may include a flexible tray having a cavity for containing the syringe. The cavity may include an opening, one or more sidewalls, and a base. A lip may surround the opening, may extend radially outward from the cavity, and may define a periphery of the tray. A removable cover may have a periphery that is adhered to the lip, and the removable cover may be permeable to a gaseous sterilant, including one or more of vaporized hydrogen peroxide or ethylene oxide. A projection may be associated with the base of the cavity and may extend away from the base of the cavity in a direction opposite to the opening of the cavity.

20 Claims, 9 Drawing Sheets

Related U.S. Application Data continuation of application No. 16/942,271, filed on Jul. 29, 2020, now Pat. No. 11,160,918.

(60) Provisional application No. 62/879,906, filed on Jul. 29, 2019.

(56) References Cited

U.S. PATENT DOCUMENTS

| | | | |
|---|---|---|---|
| 3,074,540 | A | 1/1963 | Beich et al. |
| 3,075,639 | A | 1/1963 | Lingley |
| 3,353,664 | A * | 11/1967 | Armentrout et al. . A61M 5/002 206/459.5 |
| D210,931 | S | 5/1968 | Armentrout |
| 3,403,714 | A | 10/1968 | Hulm |
| 3,420,431 | A | 1/1969 | Donovan |
| 3,435,944 | A | 4/1969 | Ishii |
| D223,187 | S | 3/1972 | Wing |
| 3,937,219 | A | 2/1976 | Karakashian |
| 4,015,709 | A | 4/1977 | Millet |
| 4,055,672 | A | 10/1977 | Hirsch et al. |
| 4,106,621 | A | 8/1978 | Sorenson |
| 4,184,593 | A | 1/1980 | Dorr |
| 4,373,631 | A | 2/1983 | Friese et al. |
| 4,497,406 | A | 2/1985 | Takanashi |
| 4,524,868 | A | 6/1985 | Buckley et al. |
| D304,157 | S | 10/1989 | Holewinski |
| 5,082,112 | A | 1/1992 | Dunklee |
| 5,156,267 | A | 10/1992 | Yates, Jr. et al. |
| 5,246,109 | A | 9/1993 | Markle |
| 5,353,929 | A | 10/1994 | Foster |
| 5,379,895 | A | 1/1995 | Foslien |
| 5,386,908 | A | 2/1995 | Sinn |
| 5,390,792 | A | 2/1995 | Van Ness et al. |
| 5,392,909 | A | 2/1995 | Hackett |
| 5,407,070 | A | 4/1995 | Bascos |
| 5,485,917 | A | 1/1996 | Early |
| 5,507,730 | A | 4/1996 | Haber et al. |
| D373,527 | S | 9/1996 | Phillips |
| 5,613,609 | A * | 3/1997 | Hamilton et al. ...... A61J 1/035 206/532 |
| 5,690,222 | A * | 11/1997 | Peters .................... B65D 77/26 206/592 |
| D395,392 | S | 6/1998 | Lahm et al. |
| 6,080,456 | A | 6/2000 | Fonteyne |
| D430,015 | S | 8/2000 | Himbert et al. |
| D440,874 | S | 4/2001 | Shurtleff et al. |
| 6,216,885 | B1 | 4/2001 | Guillaume |
| 6,228,324 | B1 | 5/2001 | Hasegawa |
| 6,523,825 | B2 | 2/2003 | Francis |
| 6,729,370 | B2 | 5/2004 | Norton et al. |
| 6,814,236 | B2 | 11/2004 | Roshdy |
| 6,915,901 | B2 | 7/2005 | Feinberg |
| 6,994,213 | B2 | 2/2006 | Giard, Jr. et al. |
| 7,055,694 | B2 | 6/2006 | Roshdy |
| D554,492 | S | 11/2007 | Bochmann et al. |
| D578,873 | S | 10/2008 | Plumer |
| 7,470,257 | B2 | 12/2008 | Norton et al. |
| D608,456 | S | 1/2010 | Sandel |
| D623,935 | S | 9/2010 | Kim et al. |
| 7,954,636 | B2 | 6/2011 | Vincent-Aubry |
| 8,042,689 | B2 | 10/2011 | Fröjd et al. |
| D661,188 | S | 6/2012 | Fahy |
| 8,303,599 | B2 | 11/2012 | Hess et al. |
| D676,323 | S | 2/2013 | Sugden et al. |
| 8,403,936 | B2 | 3/2013 | Hess et al. |
| D700,508 | S | 3/2014 | Trontel |
| 8,727,117 | B2 | 5/2014 | Maasarani |
| 8,734,420 | B2 | 5/2014 | Ariagno et al. |
| 8,770,409 | B2 | 7/2014 | Cude |
| D715,636 | S | 10/2014 | Cira |
| D715,639 | S | 10/2014 | Sumiyoshi et al. |
| 8,945,134 | B2 | 2/2015 | Hess et al. |
| 9,144,465 | B2 | 9/2015 | Hunkeler et al. |
| 9,248,229 | B2 | 2/2016 | Devouassoux et al. |
| D750,502 | S | 3/2016 | Kirchmayr et al. |
| D751,726 | S | 3/2016 | Nishioka |
| D774,885 | S | 12/2016 | Moskovich et al. |
| 9,545,473 | B2 | 1/2017 | Devouassoux et al. |
| D780,566 | S | 3/2017 | Hubner et al. |
| D781,696 | S | 3/2017 | Hubner et al. |
| D788,936 | S | 6/2017 | Schill et al. |
| D788,937 | S | 6/2017 | Schill et al. |
| 9,750,868 | B2 | 9/2017 | Tobescu |
| D806,574 | S | 1/2018 | Ozenne |
| D809,911 | S | 2/2018 | Moskovich |
| 10,065,784 | B2 | 9/2018 | Tanoguchi |
| 10,172,682 | B2 | 1/2019 | Van Der Raad-Meijer et al. |
| D841,459 | S | 2/2019 | Toledo |
| 10,214,338 | B2 | 2/2019 | Devouassoux et al. |
| 10,299,914 | B2 | 5/2019 | Glick et al. |
| 10,329,073 | B2 | 6/2019 | Tanoguchi |
| 10,390,901 | B2 | 8/2019 | Godfrey et al. |
| 10,398,361 | B2 | 9/2019 | Karpiloff |
| D873,131 | S | 1/2020 | Watanabe |
| D877,613 | S | 3/2020 | McFaul et al. |
| 10,577,165 | B2 | 3/2020 | Sadowski |
| 10,603,427 | B2 | 3/2020 | Hasumi |
| 10,646,640 | B2 | 5/2020 | Tobescu |
| 10,653,850 | B2 | 5/2020 | Ward |
| 10,729,843 | B2 | 8/2020 | Sanders et al. |
| D895,145 | S | 9/2020 | Smith et al. |
| 10,773,014 | B2 | 9/2020 | Maasarani |
| 10,781,027 | B2 | 9/2020 | Devouassoux et al. |
| 10,792,143 | B2 | 10/2020 | Distefano |
| 10,821,221 | B2 | 11/2020 | Takahashi et al. |
| D903,507 | S | 12/2020 | Fujimaki |
| D906,102 | S | 12/2020 | Cook et al. |
| D914,493 | S | 3/2021 | Folger et al. |
| D918,032 | S | 5/2021 | Smith et al. |
| D934,069 | S | 10/2021 | Cook et al. |
| 11,160,918 | B2 | 11/2021 | Cook et al. |
| 11,173,253 | B2 | 11/2021 | Sanders et al. |
| 11,214,426 | B2 | 1/2022 | Devouassoux et al. |
| D954,564 | S | 6/2022 | Kim |
| 11,369,733 | B2 | 6/2022 | Pfrang et al. |
| D961,376 | S | 8/2022 | Cook et al. |
| D961,377 | S | 8/2022 | Cook et al. |
| 11,457,992 | B2 | 10/2022 | Heede |
| 11,504,467 | B2 | 11/2022 | Hasumi et al. |
| 11,660,385 | B1 | 5/2023 | Thakore et al. |
| 11,752,225 | B2 | 9/2023 | Shieu et al. |
| 11,793,926 | B2 | 10/2023 | Cook et al. |
| 2006/0283761 | A1 | 12/2006 | Gherdan et al. |
| 2009/0012496 | A1 | 1/2009 | Tennican |
| 2009/0157008 | A1 * | 6/2009 | Vitral ..................... A61B 90/39 604/187 |
| 2009/0264829 | A1 | 10/2009 | Harris et al. |
| 2010/0181218 | A1 | 7/2010 | Beccaro et al. |
| 2012/0248005 | A1 * | 10/2012 | Bergey .................... B65B 9/045 156/69 |
| 2013/0178759 | A1 | 7/2013 | Karpiloff |
| 2014/0013718 | A1 * | 1/2014 | Maasarani ......... B65D 77/2032 206/364 |
| 2014/0215976 | A1 | 8/2014 | Maasarani |
| 2014/0346071 | A1 | 11/2014 | Genosar et al. |
| 2015/0105734 | A1 | 4/2015 | Bryant |
| 2015/0114855 | A1 | 4/2015 | Glick et al. |
| 2015/0129442 | A1 | 5/2015 | Head et al. |
| 2016/0015855 | A1 | 1/2016 | Nohara et al. |
| 2016/0375199 | A1 | 12/2016 | Ward et al. |
| 2017/0008686 | A1 | 1/2017 | Tanoguchi |
| 2017/0128662 | A1 | 5/2017 | Schill et al. |
| 2017/0143893 | A1 | 5/2017 | Hasumi et al. |
| 2017/0182240 | A1 | 6/2017 | Kerschbaumer et al. |
| 2017/0367780 | A1 | 12/2017 | Van Der Raad-Meijer et al. |
| 2017/0369198 | A1 | 12/2017 | Levy |
| 2018/0015217 | A1 | 1/2018 | Hasumi |
| 2018/0085515 | A1 | 3/2018 | Mide et al. |
| 2018/0161491 | A1 | 6/2018 | Sanders et al. |
| 2018/0264111 | A1 | 9/2018 | Pedrussio et al. |
| 2018/0311027 | A1 | 11/2018 | Distefano |
| 2019/0298513 | A1 | 10/2019 | Weber |
| 2020/0023117 | A1 | 1/2020 | Maruyama et al. |

(56) References Cited

U.S. PATENT DOCUMENTS

| | | | | |
|---|---|---|---|---|
| 2020/0164100 | A1 | 5/2020 | Nohara et al. | |
| 2020/0171244 | A1 | 6/2020 | Weikart et al. | |
| 2020/0297919 | A1 | 9/2020 | Hemminger et al. | |
| 2021/0030945 | A1 | 2/2021 | Cook et al. | |
| 2021/0077645 | A1 | 3/2021 | Mismar et al. | |
| 2021/0259828 | A1 | 8/2021 | Weber | |
| 2021/0261297 | A1 | 8/2021 | Bitong et al. | |
| 2022/0033160 | A1 | 2/2022 | Hasumi | |
| 2022/0133981 | A1 | 5/2022 | Dumont et al. | |
| 2022/0175979 | A1 | 6/2022 | Ryan et al. | |
| 2022/0323670 | A1 | 10/2022 | Foster | |
| 2023/0201483 | A1 | 6/2023 | Sanders et al. | |
| 2023/0248898 | A1 | 8/2023 | Cook et al. | |
| 2023/0293819 | A1 | 9/2023 | Genosar | |
| 2023/0310681 | A1 | 10/2023 | Hemminger et al. | |
| 2023/0310734 | A1 | 10/2023 | Tono et al. | |
| 2023/0312209 | A1* | 10/2023 | Morgan et al. | B65D 75/326 206/532 |
| 2023/0414800 | A1 | 12/2023 | Shieu et al. | |

FOREIGN PATENT DOCUMENTS

| | | | | |
|---|---|---|---|---|
| CN | 108430536 | A | 8/2018 | |
| DM | 212582 | | 1/2021 | |
| DM | 226671 | | 2/2023 | |
| EM | 0019151170001 | | 9/2011 | |
| EP | 0169154 | A1 | 1/1986 | |
| EP | 1293222 | B1 | 3/2003 | |
| EP | 1813299 | A2 | 8/2007 | |
| EP | 2155570 | B1 | 4/2015 | |
| EP | 2878320 | A1 | 6/2015 | |
| EP | 2662102 | B1 | 3/2016 | |
| EP | 2872195 | B1 | 4/2017 | |
| EP | 3178504 | A1 | 6/2017 | |
| EP | 2968729 | B1 | 8/2018 | |
| EP | 3424547 | A1 | 1/2019 | |
| EP | 3437678 | A1 | 2/2019 | |
| EP | 3124005 | B1 | 12/2019 | |
| EP | 3291856 | B1 | 1/2020 | |
| EP | 3603602 | A1 | 2/2020 | |
| EP | 3226895 | B1 | 7/2020 | |
| EP | 3687599 | A1 | 8/2020 | |
| EP | 3763384 | A1 | 1/2021 | |
| EP | 3777875 | A1 | 2/2021 | |
| EP | 3017402 | B1 | 3/2021 | |
| EP | 3866878 | A1 | 8/2021 | |
| EP | 3074069 | B1 | 11/2021 | |
| EP | 3484531 | B1 | 11/2021 | |
| EP | 3954409 | A1 | 2/2022 | |
| EP | 4031208 | A1 | 7/2022 | |
| EP | 4153494 | A1 | 3/2023 | |
| EP | 3413851 | B1 | 9/2023 | |
| EP | 4249015 | A1 | 9/2023 | |
| EP | 4255523 | A1 | 10/2023 | |
| EP | 4257509 | A1 | 10/2023 | |
| GB | 2079751 | | 6/1998 | |
| JP | S5251818 | U | 4/1977 | |
| JP | 11193010 | A * | 7/1990 | A61M 5/002 |
| JP | 11334757 | | 12/1999 | |
| JP | H11334757 | A * | 12/1999 | A61M 5/002 |
| JP | 2000159266 | A | 6/2000 | |
| JP | 1233133 | | 3/2005 | |
| JP | 1250610 | | 9/2005 | |
| JP | 1256931 | | 11/2005 | |
| JP | 2011005182 | A * | 1/2011 | A61M 5/002 |
| JP | 1481860 | | 10/2013 | |
| JP | 1493484 | | 3/2014 | |
| JP | 1661527 | | 6/2020 | |
| RU | 2225226 | C2 | 3/2004 | |
| WO | 9838109 | A1 | 9/1998 | |
| WO | D0483300001 | | 3/1999 | |
| WO | 2006064231 | A1 | 6/2006 | |
| WO | 2008154188 | A1 | 12/2008 | |
| WO | 2010081838 | A2 | 7/2010 | |
| WO | 2012043512 | A1 | 4/2012 | |
| WO | 2012158973 | A2 | 11/2012 | |
| WO | 2014004348 | A1 | 1/2014 | |
| WO | 2014014728 | A1 | 1/2014 | |
| WO | 2014045336 | A1 | 3/2014 | |
| WO | 2014122782 | A1 | 8/2014 | |
| WO | 2014136081 | A1 | 9/2014 | |
| WO | 2014140097 | A1 | 9/2014 | |
| WO | 2014187779 | A1 | 11/2014 | |
| WO | 2015000091 | A1 | 1/2015 | |
| WO | 2015078867 | A1 | 6/2015 | |
| WO | 2015147305 | A1 | 10/2015 | |
| WO | 2016021650 | A1 | 2/2016 | |
| WO | 2016087569 | A1 | 6/2016 | |
| WO | 2016101337 | A1 | 6/2016 | |
| WO | 2016159059 | A1 | 10/2016 | |
| WO | 2016177856 | A1 | 11/2016 | |
| WO | 2017139375 | A1 | 8/2017 | |
| WO | 2017158801 | A1 | 9/2017 | |
| WO | 2017169038 | A1 | 10/2017 | |
| WO | 2017220795 | A1 | 12/2017 | |
| WO | 2018015784 | A1 | 1/2018 | |
| WO | 2018111798 | A1 | 6/2018 | |
| WO | 2018111799 | A1 | 6/2018 | |
| WO | 2018181531 | A1 | 10/2018 | |
| WO | 2019063785 | A1 | 4/2019 | |
| WO | 2020078920 | A1 | 4/2020 | |
| WO | 2021021925 | A1 | 2/2021 | |
| WO | 2021056020 | A1 | 3/2021 | |
| WO | 2021237091 | A1 | 11/2021 | |
| WO | 2022119695 | A1 | 6/2022 | |
| WO | 2022124114 | A1 | 6/2022 | |
| WO | 2022202382 | A1 | 9/2022 | |
| WO | 2022216985 | A1 | 10/2022 | |
| WO | 2023041697 | A1 | 3/2023 | |
| WO | 2023147491 | A2 | 8/2023 | |
| WO | 2023150685 | A1 | 8/2023 | |
| WO | 2023180450 | A1 | 9/2023 | |
| WO | 2023235243 | A1 | 12/2023 | |

OTHER PUBLICATIONS

Colamark. RH1 High Speed Horizontal Tray Inserter. http://www.colamark.com/products/RH1_en.html.

Mivision. Eylea Pre-filled Syringe PBS Listed, Indications Expanded. Published Dec. 1, 2020. https://www.mivision.com.au/2020/12/eylea-pre-filled-syringe-pbs-listed-indications-expanded-2/.2020.

ESS Technologies. Syringe Tray Loading. https://www.esstechnologies.com/AppNotes/AB-Robotic-Tray-Loader-Syringes.shtml.

* cited by examiner

MEDICAL DEVICE PACKAGING AND RELATED METHODS

CROSS-REFERENCE TO RELATED APPLICATIONS

This application is a continuation of U.S. application Ser. No. 17/495,407, filed Oct. 6, 2021, which is a continuation of U.S. application Ser. No. 16/942,271, filed Jul. 29, 2020, which claims the benefit of priority from U.S. Provisional Application No. 62/879,906, filed Jul. 29, 2019, each of which are incorporated by reference herein in their entireties.

FIELD OF THE DISCLOSURE

Various embodiments of the present disclosure relate to packaging for a medical device. Specifically, embodiments of the disclosure may be drawn to blister packaging having a projection, e.g., a dome-shaped, bulbous, or mounded portion, associated with a base of the packaging so that the projection extends away from a device when the device is contained within the blister packaging. The projection may be used to eject the device from the blister packaging. Specifically, the projection portion may be used to flex the blister packaging to remove a syringe, e.g., a pre-filled syringe, from the blister packaging.

INTRODUCTION

Many medical devices are packaged for distribution to healthcare facilities and/or for storage, for example. Once a healthcare provider is ready to use the medical device, the medical device is removed from the packaging and prepped, if necessary, for use on a patient. In order to remove medical devices from packaging, users often need to directly handle the devices and to push, pull, lift, slide, or otherwise directly touch the medical device with their hands. In some instances, it may not be desirable to handle the medical devices too much, e.g., for reasons of sterility or to inhibit damage to the medical devices, when removing the medical devices from their packaging. For example, syringes, especially pre-filled syringes, may be contaminated when they are handled during removal of packaging, which may jeopardize the sterility of the syringe body, needle, needle attachment, and/or any medicament or other fluid contained within. If the pre-filled syringe is an ophthalmic syringe, handling during removal from packaging may lead to contamination of the syringe and/or medicament, which may in turn lead to infectious inflammation of the eye, e.g., intraocular infections, such as post-injection endophthalmitis. Additionally, in the case of pre-filled syringes, handling of the syringe may jeopardize dose accuracy, e.g., if the syringe plunger is bumped during removal from the packaging. With ophthalmic syringes, dose accuracy may be more important, because the dose size may be relatively small, e.g., less than or equal to 20 ml, less than or equal to 15 ml, less than or equal to 10 ml, less than or equal to 0.5 ml, or less than or equal to 1 ml. For example, the dose may be less than or equal to 200 μl, less than or equal to 150 μl, or less than or equal to 100 μl. Accordingly, there exists a need for medical device packaging that decreases the amount of direct handling of the medical device, particularly pre-filled ophthalmic syringes, during removal from the packaging.

SUMMARY

According to one aspect of the disclosure, packaging for a sterile syringe having a nominal size of less than 1 mL may include a tray having a cavity for containing the syringe. The cavity may include an opening, one or more sidewalls, and a base. A lip may surround the opening, may extend radially outward from the cavity, and may define a periphery of the tray. A removable cover may have a periphery that is adhered to the lip, and the removable cover may be permeable to a gaseous sterilant, including one or more of vaporized hydrogen peroxide or ethylene oxide. A projection may be associated with the base of the cavity and may extend away from the base of the cavity in a direction opposite to the opening of the cavity. The projection may be made of a deformable material.

Various embodiments of the packaging may include one or more of the following aspects: the projection may be dome-shaped, and a diameter of a base of the dome-shaped projection may be approximately 10 mm to 20 mm; the cavity may include three cavity portions arranged in series along a longitudinal axis of the tray, and the three cavity portions may be connected to each other via narrowed portions; the projection may be associated with a middle cavity portion of the three cavity portions, and wherein the tray may be formed from a suitable thermoplastic material, including one or more of polypropylene, polystyrene, polyethylene, polycarbonate, polyvinyl chloride, or polyethylene terephthalate glycol; when the sterile syringe is contained within the cavity, a height of the projection from an apex of the projection to a base of the projection may be approximately 5 mm to 6 mm, and a distance between the base of the projection and a portion of the syringe overlying the projection may be approximately 3 mm to 4 mm; the sterile syringe may be a pre-filled syringe; the tray may include at least two geometrical features located on at least one sidewall of the packaging to retain the syringe within the cavity by friction fit; or the tray may include a third geometrical feature located on the base of the cavity below where the sterile syringe is to be contained within the cavity.

In another aspect, the present disclosure includes packaging comprising a tray having an opening and a cavity, wherein the cavity includes a plurality of sidewalls and a base. A sterile syringe may be contained within the cavity, and the sterile syringe may be pre-filled with a medicament. A bulbous projection may be associated with the tray at a location in line with a portion of the sterile syringe. In a first state, the bulbous projection may extend away from the sterile syringe in a direction opposite from the opening of the cavity, and, in a second state, the bulbous projection may be inverted so that a portion of the bulbous projection extends towards the portion of the sterile syringe in line with the bulbous projection. The bulbous projection may be configured to transition from the first state to a second state when subjected to pressure.

Various embodiments of the packaging may include one or more of the following aspects: the bulbous projection may underlie a barrel of the sterile syringe when in the first state; the cavity may include three cavity portions, wherein a first cavity portion contains a plunger of the sterile syringe, a second cavity portion contains a barrel of the sterile syringe, and a third cavity portion contains a distal portion of the sterile syringe; the three cavity portions may be connected to one another by intermediate narrowed portions, and the sterile syringe may extend through the narrowed portions; the narrowed portions may include a plurality of geometric features projecting into the narrowed portions to retain the sterile syringe in the cavity via friction fit; the packaging may include a removable cover sealing an opening of the cavity opposite the base, and the removable cover may be permeable to a gaseous sterilant and configured to maintain a sterile barrier; or the medicament may be one of aflibercept, ranibizumab, bevacizumab, conbercept, OPT-302, RTH258 (brolucizumab), a pegylated designed ankyrin repeating protein (DARPin), or RG7716.

In another aspect, the present disclosure is drawn to a method of removing an externally-sterilized syringe from packaging. The method may include peeling off a removable cover from a blister packaging tray having a cavity configured to receive the externally-sterilized syringe therein, wherein the blister packaging tray includes a dome-shaped projection associated with a base of the cavity of the blister packaging tray and aligned with the externally-sterilized syringe. The method may further include pushing a portion of the dome-shaped projection towards the cavity of the blister packaging tray, wherein pushing the portion of the dome-shaped projection causes a portion of the blister packaging tray to flex. The method may also include orienting the blister packaging tray so that an opening of the cavity faces a sterile surface to discharge the externally-sterilized syringe from the blister packaging tray and onto the sterile surface.

Various embodiments of the method may include one or more of the following aspects: the externally-sterilized syringe may be pre-filled with aflibercept, ranibizumab, bevacizumab, conbercept, OPT-302, RTH258 (brolucizumab), a pegylated designed ankyrin repeating protein (DARPin), or RG7716; the blister packaging tray may be fabricated from a material including one or more of polypropylene, polystyrene, polyethylene, polycarbonate, polyvinyl chloride, or polyethylene terephthalate glycol; the removable cover may be permeable to a gaseous sterilant; and the gaseous sterilant may be vaporized hydrogen peroxide or ethylene oxide.

In another aspect, the present disclosure is drawn to a method of removing an externally-sterilized syringe from a packaging, the packaging including a tray having a cavity, a deformable projection associated with the cavity, and an opening covered by a gas-permeable material. The method may include removing the gas-permeable material so as to expose the opening of the tray, deforming the projection into the cavity and toward a barrel of the externally-sterilized syringe, wherein the step of deforming the projection also causes a portion of the tray to flex, and ejecting the externally-sterilized syringe from the tray.

Various embodiments of the method may include one or more of the following aspects: ejecting the externally-sterilized syringe from the tray may be performed without a user directly handling the syringe; the gas-permeable material may be permeable to vaporized hydrogen peroxide or ethylene oxide; the deformable projection may include a bulbous shape; or the externally-sterilized syringe may be pre-filled with aflibercept, ranibizumab, bevacizumab, conbercept, OPT-302, RTH258 (brolucizumab), a pegylated designed ankyrin repeating protein (DARPin), or RG7716.

In another aspect, the present disclosure is drawn to a method of removing an externally-sterilized syringe from a packaging, the packaging including a tray having a cavity, and an opening covered by a gas-permeable material. The method may include removing the gas-permeable material so as to expose the opening of the tray, deforming a portion of the cavity toward a barrel of the externally-sterilized syringe, so as to cause a portion of the tray to flex, and ejecting the externally-sterilized syringe from the tray.

Various embodiments of the method may include one or more of the following aspects: ejecting the externally-sterilized syringe from the tray may be performed without a user touching the externally-sterilized syringe with a bare hand; the gas-permeable material may be permeable to one or more of vaporized hydrogen peroxide or ethylene oxide; or the externally-sterilized syringe may be pre-filled with aflibercept, ranibizumab, bevacizumab, conbercept, OPT-302, RTH258 (brolucizumab), a pegylated designed ankyrin repeating protein (DARPin), or RG7716.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

Figure 1:
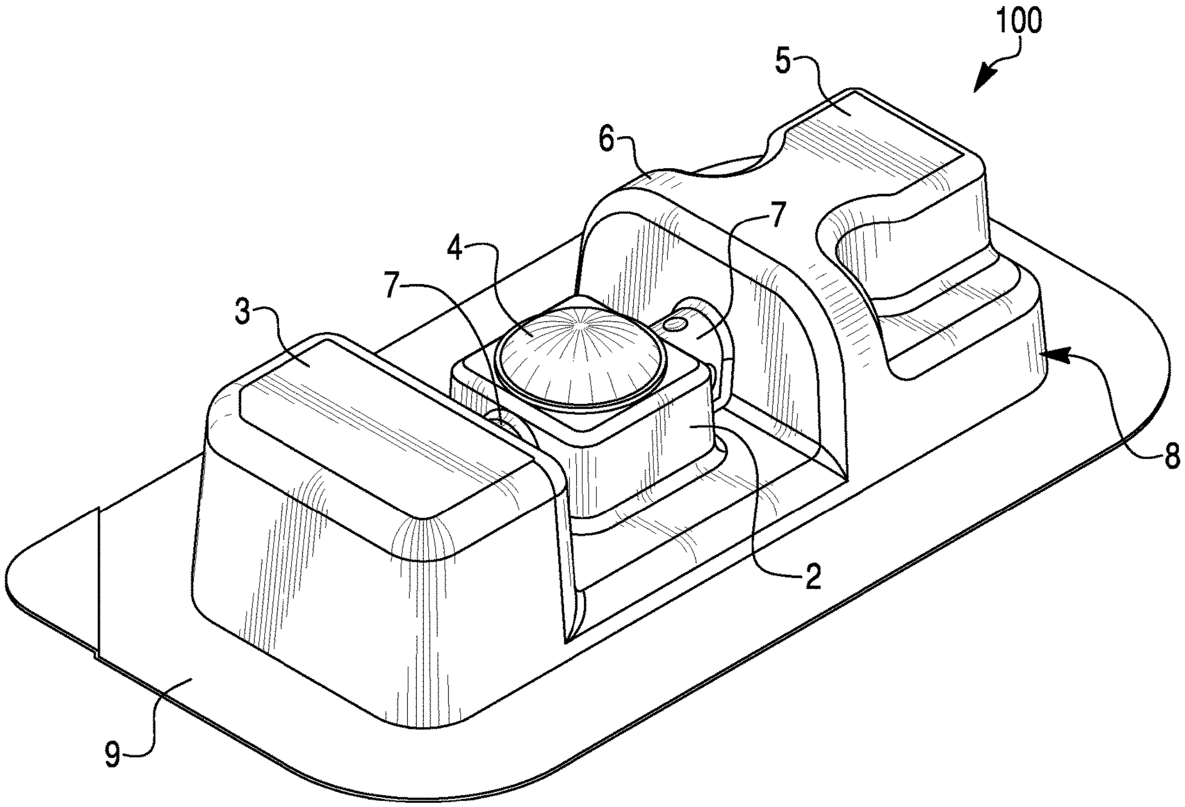
FIG. 1 provides a perspective view of exemplary packaging, according to an embodiment of the present disclosure.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items.

The term "distal end," or any variation thereof, refers to the portion of a device farthest from an operator of the device during an injection operation. For example, the distal end of a syringe would be the needle end of the syringe. Conversely, the term "proximal end," or any variation thereof, refers to the portion of the device closest to a the operator of the device during an injection operation. For example, the proximal end of a syringe would be the plunger end of the syringe. Further, as used herein, the terms "about," "substantially," and "approximately" generally mean+/−10% of the indicated value.

As used in the present disclosure, the term "sterilization" refers to achieving a level of sterility appropriate for a formulated drug substance or drug product for commercial distribution and use. Such a level of sterility may be defined in, for example, regulatory guidelines or regulations, such as guidelines released by the U.S. Food and Drug Administration. In some embodiments, such a level of sterility may include, for example, a 6-log reduction in microbial populations of biological indicators placed on an outside or inside surface of a drug product (e.g., an outside surface of a syringe or an inside surface of a blister pack). In other embodiments, such a level of sterility may include, for example, a 9-log or 12-log reduction in microbial populations of biological indicators. Sterilization refers to achieving such an appropriate level of sterility while also achieving a sufficiently low level of residual sterilizing chemicals (e.g., vaporized hydrogen peroxide, ethylene oxide, etc.) for commercial distribution and use. Such a low level of residual sterilizing chemical may also be defined in regulatory guidelines or regulations.

As used in the present disclosure, the term "external sterilization" refers to the sterilization of a drug delivery device in a container or packaging, such as in a primary packaging component, or in both primary and secondary packaging components, suitable for commercial distribution and use.

DETAILED DESCRIPTION

Embodiments of the present disclosure relate to medical device packaging, and, in particular, to packaging for syringes (e.g., pre-filled syringes). In some embodiments, the packaging may be configured to contain externally-sterilized syringes. In particular, embodiments of the disclosure may be directed to packaging for externally-sterilized, pre-filled syringes containing ophthalmic medicaments. Exemplary ophthalmic syringes may be pre-filled with, e.g., 50 mL or less, 20 mL or less, 15 mL or less, 10 mL or less, 5 mL or less, or 1 ml or less of an ophthalmic medicament. In some embodiments, exemplary packages may have a nominal size of less than 1 mL. Exemplary syringes are described in PCT/US2020/036200, which is incorporated by reference herein in its entirety. The packaging may include one or more features to facilitate removal of a medical device from the packaging. For example, the packaging may include one or more deformable projection portions that may be inverted, pushed, and/or otherwise deformed in order to dislodge, eject, push, or otherwise move the medical device to release it from the packaging. The packaging may also be flexible to allow a user to push on the projection to bend or flex the packaging to promote release of the medical device contained within.

In some exemplary embodiments, the deformable portion(s) may include a projection, e.g., a dome mound, or other bulbous projection, associated with a base of the packaging over which a medical device, e.g., a syringe, is configured to be positioned when the medical device is contained within the packaging. The projection may extend outwards away from where the medical device is configured to be located and may be accessible from an outer surface of the packaging.

To facilitate removal of the medical device from the packaging, a user may orient the packaging so that an opening of the packaging is angled toward a surface onto which the medical device is to be ejected. A user may also push on the projection to flex the packaging so that a central portion of the packaging bends towards the medical device while one or more edges of the packaging bend away from the medical device. For example, the user may push on the projection and turn the packaging sideways or up-side-down while flexing the packaging in order to discharge the syringe from the tray and onto a sterile surface, e.g., a sterile table, tray, cloth, liner, etc. Flexure of the packaging while an opening of the packaging is angled gravitationally downward may cause medical device to be released, e.g., ejected, out of the packaging onto a surface with the user contacting only the packaging and not directly contacting the medical device.

Pushing on the projection may also at least partially invert the projection. The inverted part of the projection may or may not contact the medical device contained within the packaging to help push the medical device out of the packaging. In some embodiments, pushing on the projection to flex the packaging may be enough to eject the device, while in others, the inverted projection may push on a portion of the medical device (e.g., a barrel of a syringe) to facilitate ejection of the device from the packaging. Indeed, the projection may function as a central landmark or target for a user to push on in order to flex the packaging to eject the device. The projection may include, e.g., an arrow or other visual identifier to indicate to a user to push on the packaging in a central location in order to flex the packaging to eject the syringe. Exemplary aspects of the packaging are described in further detail herein.

FIG. 1 shows a bottom view of exemplary packaging 100 for a medical device. Specifically, packaging 100 may be designed to contain a drug-delivery device such as a syringe, e.g., a pre-filled syringe. Exemplary pre-filled syringes may be used with any therapies for ophthalmic diseases, including for the treatment of patients with Neovascular (Wet) Age-related Macular Degeneration (AMD), Macular Edema following Retinal Vein Occlusion (RVO), Diabetic Macular Edema (DME), and/or Diabetic Retinopathy (DR). In particular, large molecule and small molecule antagonists of VEGF and/or ANG-2, such as aflibercept (Eylea®), ranibizumab (Lucentis®), bevacizumab (Avastin®), conbercept, OPT-302, RTH258 (brolucizumab), a pegylated designed ankyrin repeating protein (DARPin) like abicipar pegol, or RG7716 may be used with exemplary syringes. Embodiments of the present disclosure may also be used for cosmetic applications or medical dermatology, such as treatment or diagnosis of allergic responses. Packaging 100 includes a tray 8, in which the syringe is contained during storage, and a lip 9 extending around a perimeter of tray 8 and defining an opening in tray 8. The top of tray 8 (shown in FIG. 4) may be sealed with a removable cover 28 (FIG. 3A), which may enclose the syringe within tray 8 during sterilization and/or storage. In some embodiments, packaging 100 may be blister packaging, i.e., packaging 100 may be a pre-formed plastic packaging, and tray 8 may be made from a formable web, such as a thermoformed plastic.

Packaging 100 may be suitable for use with an external sterilization process, e.g., a vapor hydrogen peroxide (VHP) sterilization process and/or an ethyl alcohol sterilization process. Accordingly, a medical device (e.g., a pre-filled syringe) may be packaged within packaging 100 and then subjected to external sterilization. Sterilants, such as VHP, may not affect the medication contained within the syringe but may sterilize the exterior surface of the syringe. Exemplary sterilization processes are described in PCT/US2018/021013, which is incorporated by reference herein in its entirety. Materials used in packaging 100 may be semi-permeable to sterilizing agents to allow the sterilizing agents to traverse portions of or all of packaging 100 to sterilize the exterior of the medical device contained within packaging 100, as well as the interior of packaging 100, once the medical device is sealed within packaging 100. For example, at least 75%, at least 80%, at least 85%, at least 90%, or at least 95%, of packaging 100 is sterilized. For example, a removable cover 28 (FIG. 3A) may be permeable to vapor hydrogen peroxide and/or an ethyl alcohol. Cover 28 may be formed of, e.g., Tyvek or other suitable high-density polyethylene fibers, ethylene-vinyl acetate, and/or other thermoplastic materials. In some embodiments, tray 8 may include an indicator to allow a user to determine whether tray 8 and its contents have been sterilized. For example, tray 8 may include an indicator (e.g., a tape or a label) that changes appearance in color or pattern to visually show whether a sterilization process has been performed.

Designing packaging 100 to be used with external sterilization processes and to allow a user to remove the contents of packaging 100 without directly handling the contents, as described herein, reduces the likelihood that sterility of the contained medical device will be compromised. As a result, packaging 100, as described herein, may also reduce the chance that a person on whom the medical device is used will be infected by the medical device. For example, if packaging 100 contains an ophthalmic syringe, packaging 100 may decrease the risk of a person getting an eye infection, e.g., intraocular infections like post-injection endophthalmitis, as a result of a contaminated syringe.

An externally-sterilized syringe may be one in which any viable organisms on the surface of the syringe have been terminated or killed, making them non-viable even though they may remain. The external surface(s) of the syringe plunger rod, flange, trailing surface of the piston, and the interior of the syringe barrel behind the syringe piston, and any other external surfaces of the syringe may be externally-sterilized. In some aspects, depyrogenation and/or other removal processes may be undertaken prior to external sterilization.

Tray 8 may include a cavity 3 configured to contain a distal portion of a syringe. The distal end of the syringe may include e.g., a luer lock and/or a syringe attachment to which a needle may be coupled once the syringe is removed from tray 8 for use. In other embodiments, the needle may already be coupled to the syringe within packaging 100 and may be further covered by a cap during storage in packaging 100. A cavity 2 may be configured to contain at least a portion of the syringe barrel (which may be a glass or plastic material compatible with the sterilant), and a cavity 5 configured to contain a flange and/or plunger of the syringe. Cavity 5 may be shaped to correspond to the shape of a flange and/or plunger of the syringe, as shown in FIG. 1. For example, flange portion 6 of cavity 5 may correspond to the shape of a flange. Comparing FIGS. 1, 5, and 7, the shape and/or sidewalls of flange portion 6 of cavity 5 may be rounded to contain a flange of the syringe. Comparing FIGS. 2, 6, and 8, an interior region of flange portion 6 of cavity 5 may be configured, e.g., to include rounded sidewalls, to contain a flange of the syringe.

Figure 5:
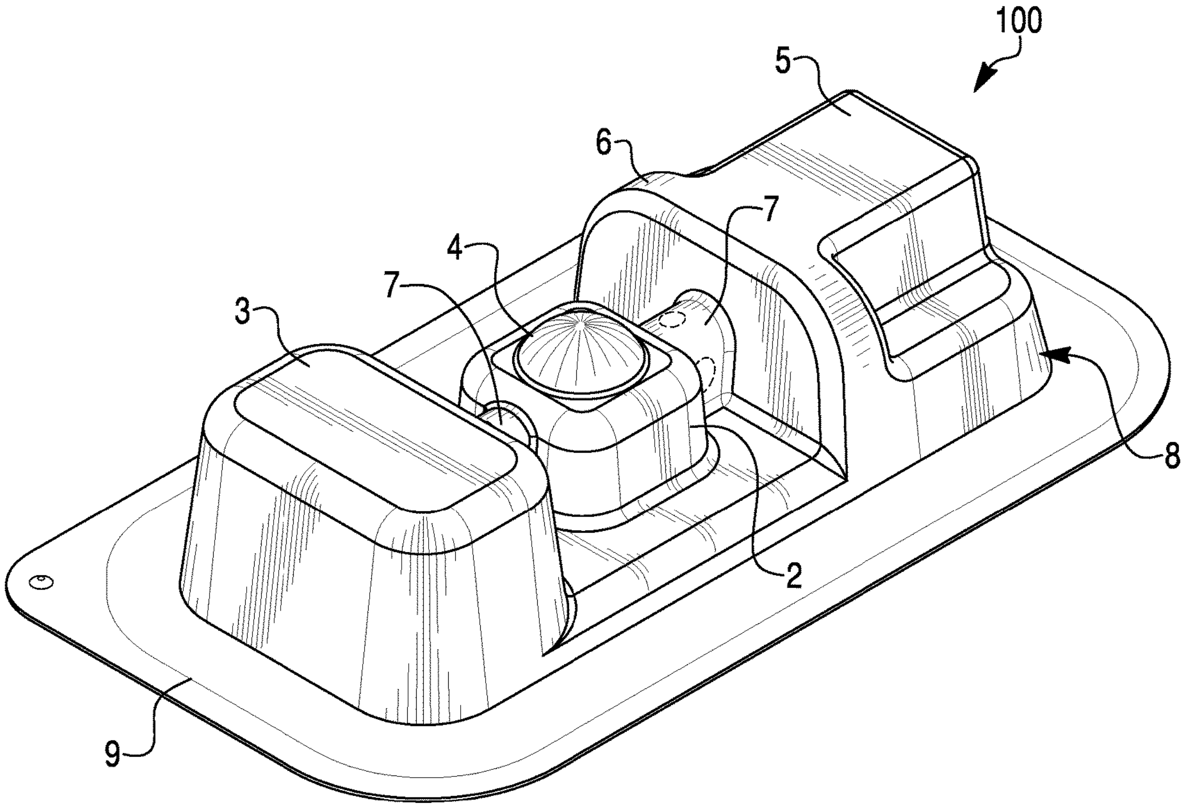
FIG. 5 provides a perspective view of exemplary packaging, according to an embodiment of the present disclosure.
Figure 6:
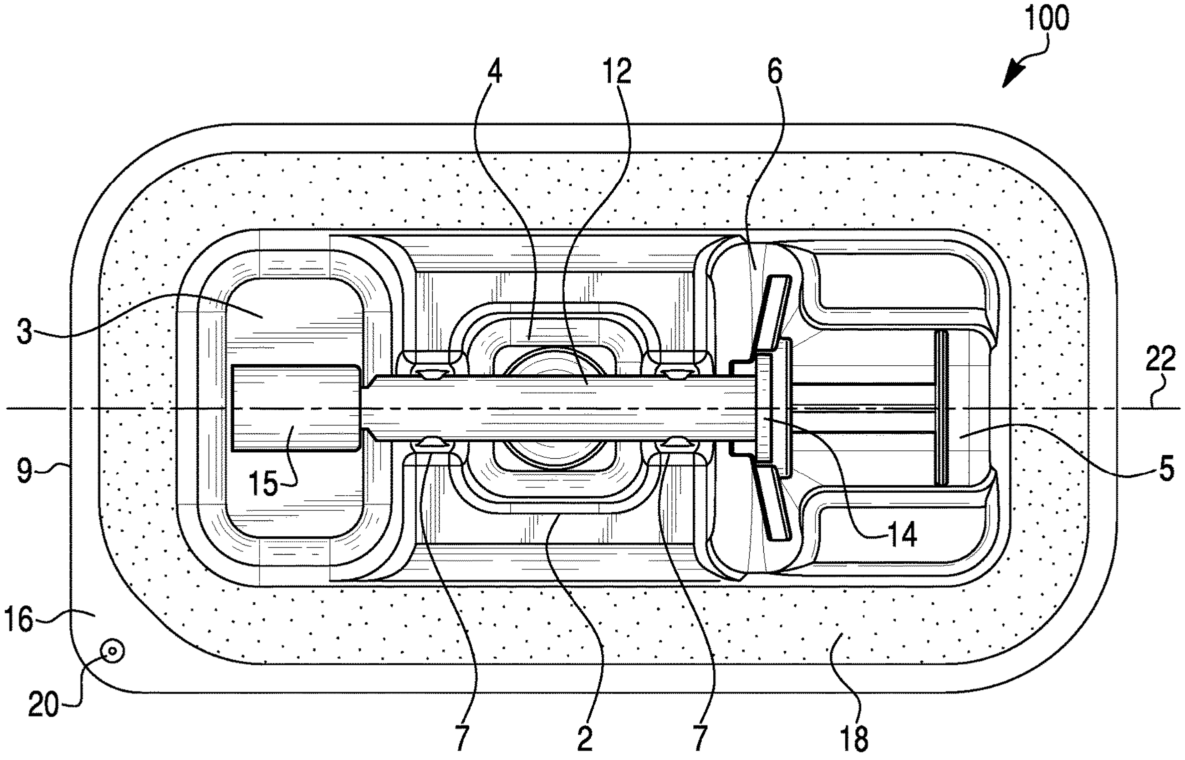
FIG. 6 provides a bottom view of exemplary packaging containing a syringe, according to an embodiment of the present disclosure.
Figure 7:
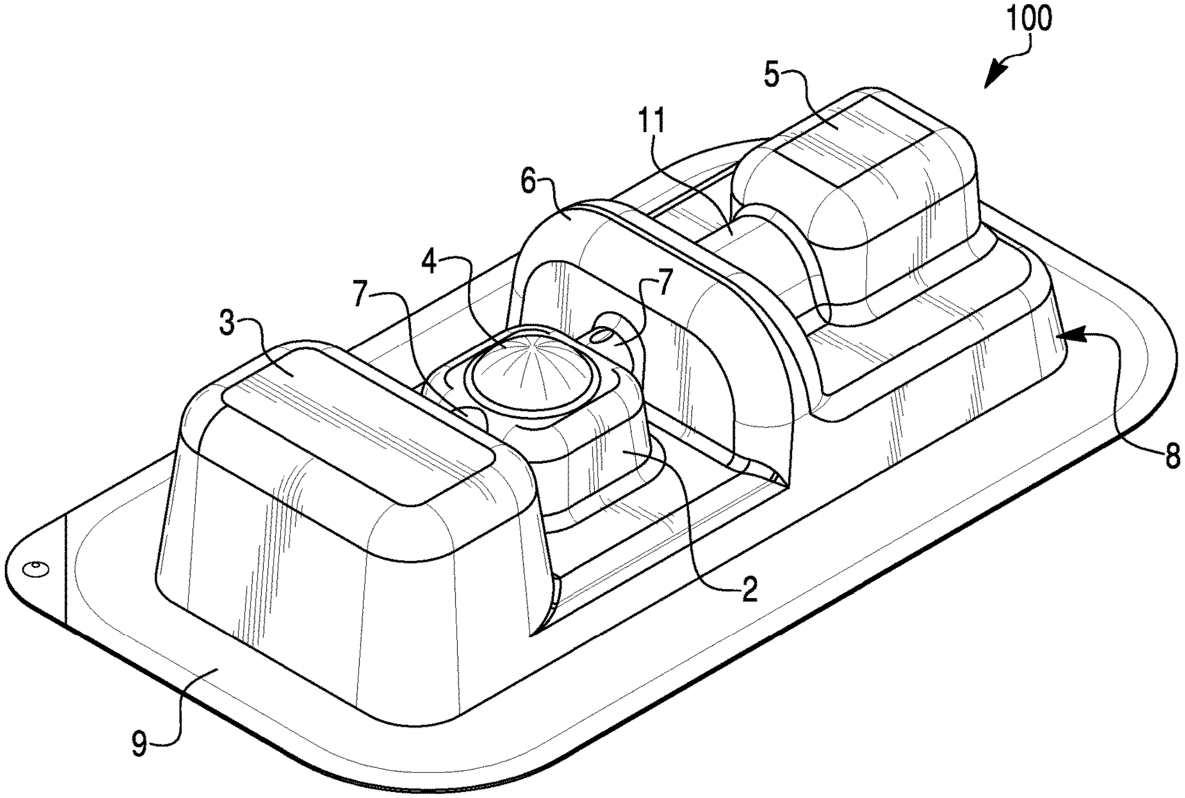
FIG. 7 provides a perspective view of exemplary packaging, according to an embodiment of the present disclosure.
Figure 8:
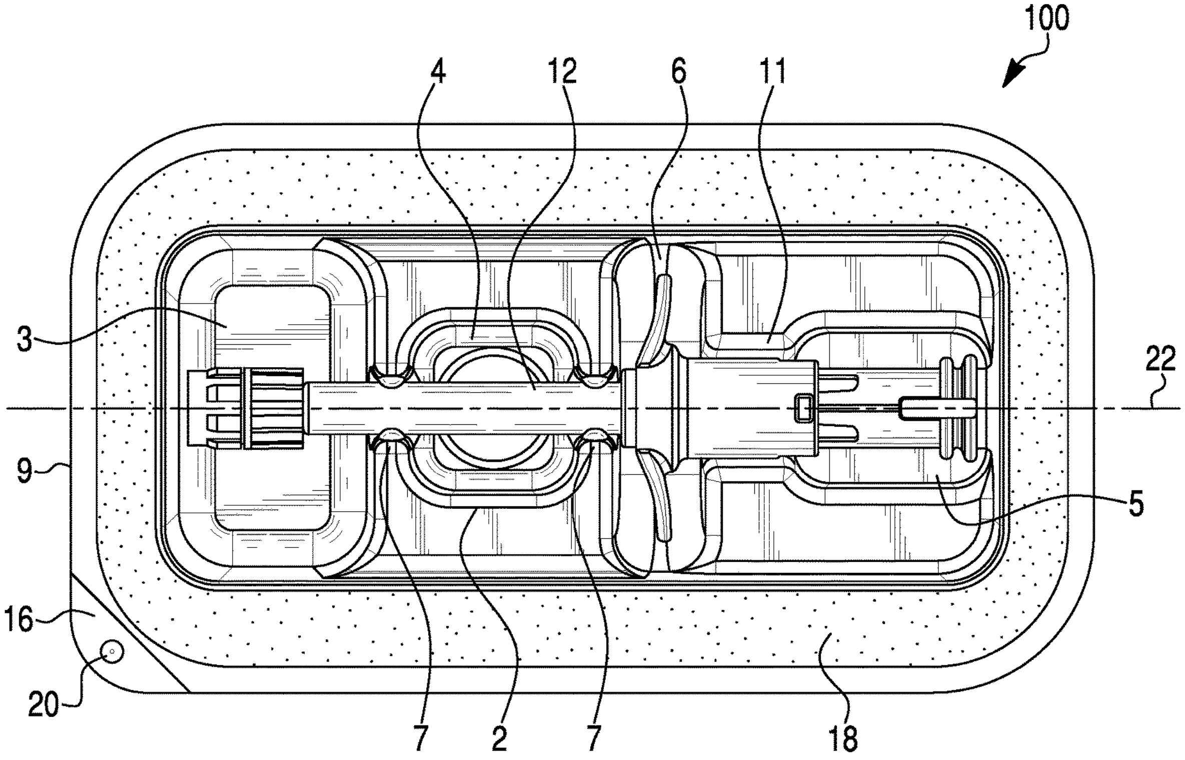
FIG. 8 provides a bottom view of exemplary packaging containing a syringe, according to an embodiment of the present disclosure.

In some aspects, a syringe contained within tray 8 may include a larger, e.g., wider plunger rod, or larger portions of a plunger rod, compared to a standard syringe, to increase the stability of a clinician's hand when pushing the plunger rod, e.g., for intravitreal injection (FIGS. 7 and 8). In such aspects, packaging 100 may be sized and shaped to accommodate the larger plunger rod. If a syringe contained within tray 8 includes a protective plunger stop, cover, and/or other element to prevent movement of the syringe plunger and/or dispensing of medicament within the syringe, then cavity 5 may be shaped to reflect the contours of a flange and/or plunger with the protective element in place. In other embodiments, however, cavity 5 may be substantially rectangular, oval, or any other suitable shape, so long as an interior region of cavity 5 defines a space large enough to contain a proximal portion of the syringe, and, if included, any accompanying protective elements. For example, FIGS. 5 and 6 show exemplary embodiments where the longitudinal side walls of cavity 5 are generally planar and parallel to at least a portion of the plunger rod of the syringe. FIGS. 7 and 8 show exemplary embodiments where cavity 5 may include recessed portion 11 shaped to correspond to a shape of at least a portion of the flange or plunger, e.g., a protective plunger stop, cover, and/or other element to prevent movement of the syringe plunger and/or dispensing of medicament within the syringe. For example, recessed portion 11 may be between a main region of cavity 5 and flange portion 6. In exemplary embodiments, for example, FIG. 5, the shape of cavity 5 may be sized to facilitate high speed manufacturing of packaging 100 and/or improve material distribution of packaging 100.

Similarly, although cavity 3 is shown as substantially rectangular and cavity 2 is shown as generally a square in the exemplary embodiment of FIG. 1, cavity 3 and cavity 2 may be of any suitable size and/or shape so as to contain a distal end of the syringe (and any cover associated with the distal end) and at least a portion of a syringe barrel, respectively. For example, cavities 2 and 3 may be an oval, circle, trapezoid, or a wider or narrower rectangle, or any combination thereof. Cavities 2, 3, 5 may be dimensioned to provide space between the walls of the cavities and the syringe to allow a sterilant to circulate within packaging 100 during a sterilization process in order to sterilize the internal surfaces of packaging 100 and the external surfaces of the syringe. Further, tray 8 and cavities 2, 3, 5 may have substantially flat surfaces on the top and bottom (e.g., cover 28 and the base) to allow multiple packages to be stacked on top of each other during storage. Flat surfaces may also allow for consistent placement in an autoclave. That said, in some embodiments, cavities 2, 3, 5 and tray 8 may have a rounded, e.g., cylindrical shape, or any other suitable shape. Further, tray 8 may have rounded or sharp corners and/or edges. In exemplary embodiments, for example, referring to FIG. 5, the shape and/or size of cavities 2, 3, 5, and tray 8 may be shaped and/or sized to facilitate high speed manufacturing of packaging 100 and/or improve material distribution of packaging 100.

Figure 2:
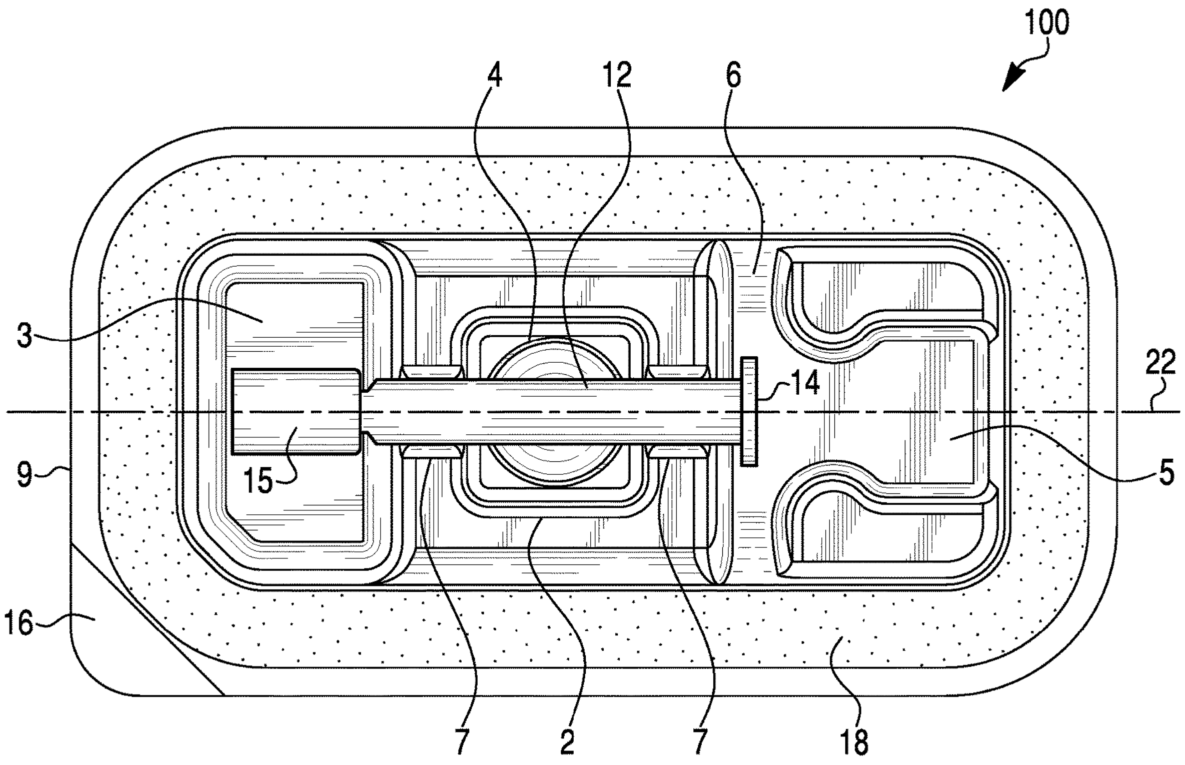
FIG. 2 provides a bottom view of exemplary packaging containing a syringe, according to an embodiment of the present disclosure.

In the embodiments of FIGS. 1, 5, and 7, narrowed portions 7 extend between cavity 2 and cavities 3, 5, fluidly coupling all three cavities. Narrowed portions 7 are dimensioned to contain regions of the syringe barrel within them, allowing the syringe to extend into all three cavities when housed within packaging 100, as can be seen in FIGS. 2, 6, and 8. For example, in FIGS. 2, 6, and 8, as described above, a plunger flange 14 of the packaged syringe lies within a flange portion 6 of cavity 5, syringe barrel 12 extends within narrowed portions 7 and across cavity 2, and a distal region of the syringe, at least partially covered by a guard 15 (e.g., a luer lock), lies within cavity 3.

Although tray 8 is shown as including three cavities 2, 3, 5, extending along a longitudinal axis 22 (FIGS. 2, 6, and 8) and connected to one another by narrowed portions 7, it is contemplated that tray 8 may have any suitable number of cavities. For example, one cavity of substantially equal depth may be included to hold a medical device, two cavities may be included, or more than three cavities may be included. Each of the cavities (in embodiments with multiple cavities) may be connected to one another so that they may in combination contain a medical device. Or, if multiple medical devices or multiple components are housed in tray 8, then tray 8 may include multiple cavities not connected to one another. In such embodiments, it is contemplated that more than one of the cavities may include a projection to facilitate removal of the medical device(s) and/or component(s) from tray 8, as will be described further below.

In the embodiment of FIGS. 1 and 2, cavity 2 includes a dome 4 on a bottom portion of packaging 100. Dome 4 may be a flexible, hollow projection in tray 8 configured to facilitate removal of a syringe from packaging 100. Dome 4 is associated with the base of cavity 2 so that dome 4 is oriented beneath the syringe when the syringe is housed within packaging 100. In the embodiment of FIG. 2, dome 4 is aligned with a central region of syringe barrel 12. Dome 4 may be made of a compressible material that deforms under pressure, e.g., pressure applied by a user. Dome 4 may be made of the same material as the rest of tray 8 or may be formed of a different, e.g., a relatively more flexible material. In some embodiments, as discussed above, dome 4 and tray 8 may be thermoformed plastic. For example, dome 4 and/or tray 8 may be formed of polypropylene, polystyrene, polyethylene, polycarbonate, polyvinyl chloride, or polyethylene terephthalate glycol (PETG). A diameter of a base of dome 4 (e.g., the widest portion of dome 4 where it meets the base of tray 8) may be approximately 10 mm to 20 mm, for example, approximately 10 mm, approximately 11 mm, approximately 12 mm, approximately 13 mm, approximately 14, approximately 15 mm, approximately 16 mm, approximately 17 mm, approximately 18 mm, or approximately 19 mm. Referring to FIG. 5, as compared to FIG. 1, a diameter of a base of dome 4 may be sized in order to facilitate high speed manufacturing of packaging 100 and/or improve material distribution of packaging 100.

Figure 3A:
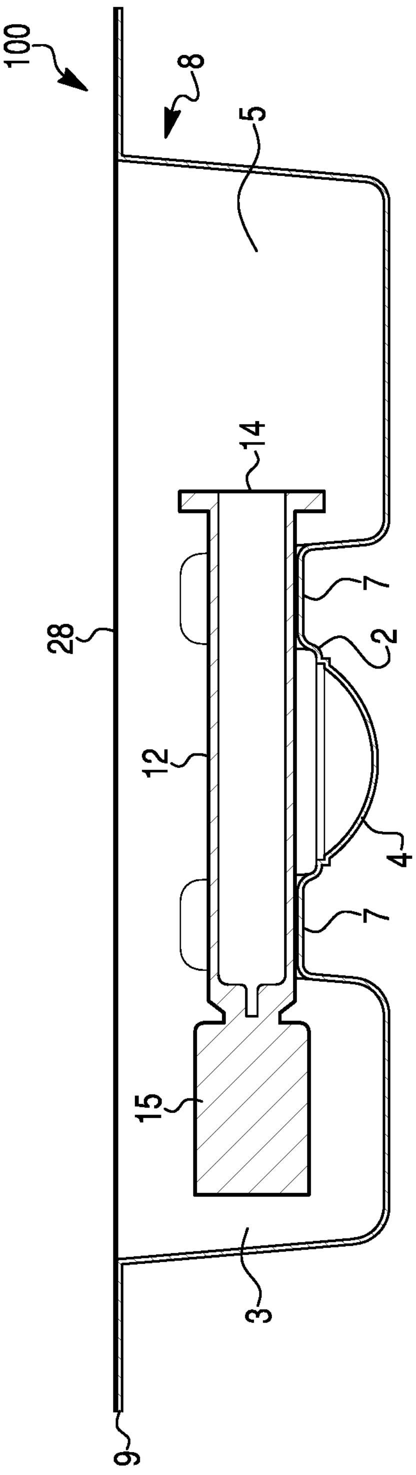
FIG. 3A provides a cross-sectional view of the packaging of FIG. 2 containing a syringe, according to an embodiment of the present disclosure.
Figure 3B:
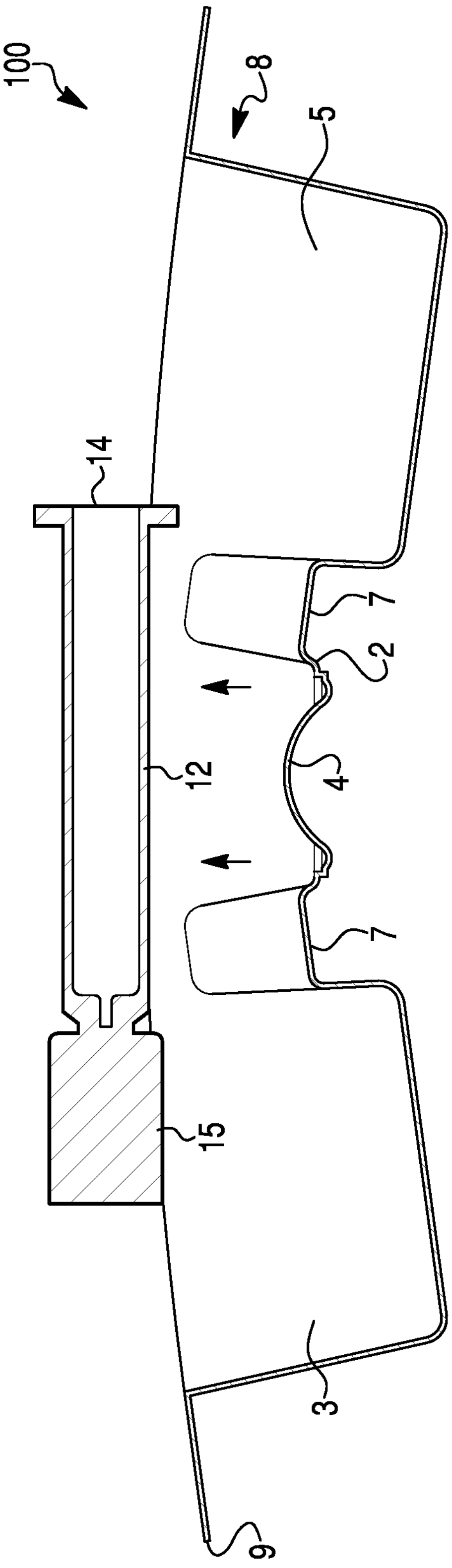
FIG. 3B provides a cross-sectional view of the packaging of FIG. 2 containing a partially ejected syringe while in a flexed configuration, according to an embodiment of the present disclosure.

FIG. 3A depicts a cross-sectional view of tray 8 containing a syringe (e.g., an empty or a pre-filled syringe containing an ophthalmic medicament). As discussed above, dome 4 projects outwards from the base of tray 8 away from the syringe when the syringe is received in tray 8, and dome 4 is aligned with and underneath (or over, depending on the orientation of tray 8) syringe barrel 12. To remove the syringe from packaging 100, removable cover 28 may be removed, e.g., peeled off, tray 8 may be turned sideways or up-side-down to position an opening of the packaging towards a surface, and dome 4 may be pushed by a user. A user may push dome 4 with one or more fingers, e.g., a thumb, towards the syringe housed within the packaging. As the user pushes on dome 4, the packaging may flex so that a central portion of the packaging bends towards the medical device while one or more edges of the packaging bend away from the medical device. As packaging 100 flexes (FIG. 3B), this may cause the syringe to be dislodged from the packaging. Because packaging 100 is oriented with an opening facing gravitationally downwards (or at least perpendicular relative to a surface below), the syringe may be ejected out of packaging 100 and onto the surface. Accordingly, pushing dome 4 and causing packaging 100 to flex may allow the user to remove the syringe from packaging 100 without ever directly touching the syringe. When packaging 100 is held upside down, the syringe may not fall out on its own, and packaging 100 may suspend and retain the syringe until a user flexes packaging 100, e.g., by pushing dome 4.

When a user pushes dome 4 to flex tray 8, dome 4 may deform and may at least partially invert. As dome 4 inverts, it may or may not be configured to contact syringe barrel 12. In some embodiments, dome 4 may push on syringe barrel 12 to help expel the syringe from packaging 100. In such embodiments, a height of dome 4 from the apex of dome 4 to the base of the cavity from which dome 4 extends may be greater than a distance from the base of the cavity to where the medical device (e.g., syringe) is positioned within tray 8. As used herein, the term "apex" refers to a portion of dome 4 that is furthest away from the base of the cavity from which dome 4 extends, irrespective of the relative orientation of dome 4 and tray 8. In an exemplary embodiment, the syringe may be contained within tray 8 so that a height of dome 4 from an apex of dome 4 to the base of tray 8 is approximately 5 mm to 6 mm, and wherein a distance between the base of tray 8 and a bottom portion of the syringe overlying dome 4 is approximately 3 mm to 4 mm. In other embodiments, however, dome 4 may not contact syringe barrel 12 when pressed by a user. Instead, the flexure of tray 8 caused by pressing dome 4 combined with orienting an opening of tray 8 gravitationally downwards may be enough to dislodge the syringe from tray 8 and to cause the syringe to be ejected onto the surface (preferably a sterile surface).

A user may push dome 4 to flex tray 8 before, during, and/or after orienting tray 8 so that an opening of tray 8 faces downwards or sideways toward a surface onto which the syringe is to be ejected (i.e., turning tray 8 so that an opening faces gravitationally downwards). Orienting the tray with an opening towards the surface may allow the syringe to fall out from tray 8 onto a suitable sterile surface without the user directly handling the syringe in order to remove the syringe from its packaging. Decreasing the amount that a user handles the syringe may decrease the possibility that the syringe and/or its contents become contaminated and infect the portion of the body that the contents of the syringe are injected into. For example, sterile ophthalmic syringes may be contained within packaging 100, and dome 4 and packaging 100 may allow a user to not jeopardize sterility when removing the syringe, which may ultimately decrease the risk of eye infections, e.g., post-injection endophthalmitis, due to contaminated syringes. Decreasing handling of the syringe may also decrease the risk of accidentally discharging some of the medicament from the syringe when removing the syringe from packaging 100.

The location of projections like dome 4 and/or other projection portions on tray 8 may not only facilitate removal of the syringe but may also guide a user on how to handle certain portions of packaging 100 when removing the syringe from packaging 100. For example, in some embodiments, dome 4 or other portions of packaging 100 may include markings, indicia, and/or tactile features (e.g., ridges, bumps, or grooves) indicating to a user where to push in order to flex tray 8 and dislodge the syringe from packaging 100. Overall, inclusion of dome 4 or other suitable projections in tray 8 may decrease one or more of the likelihood of injury to a user, damage to the device, loss of sterility of the device or any medicament therein, and/or accidental discharge of medicament within the device.

Figure 4:
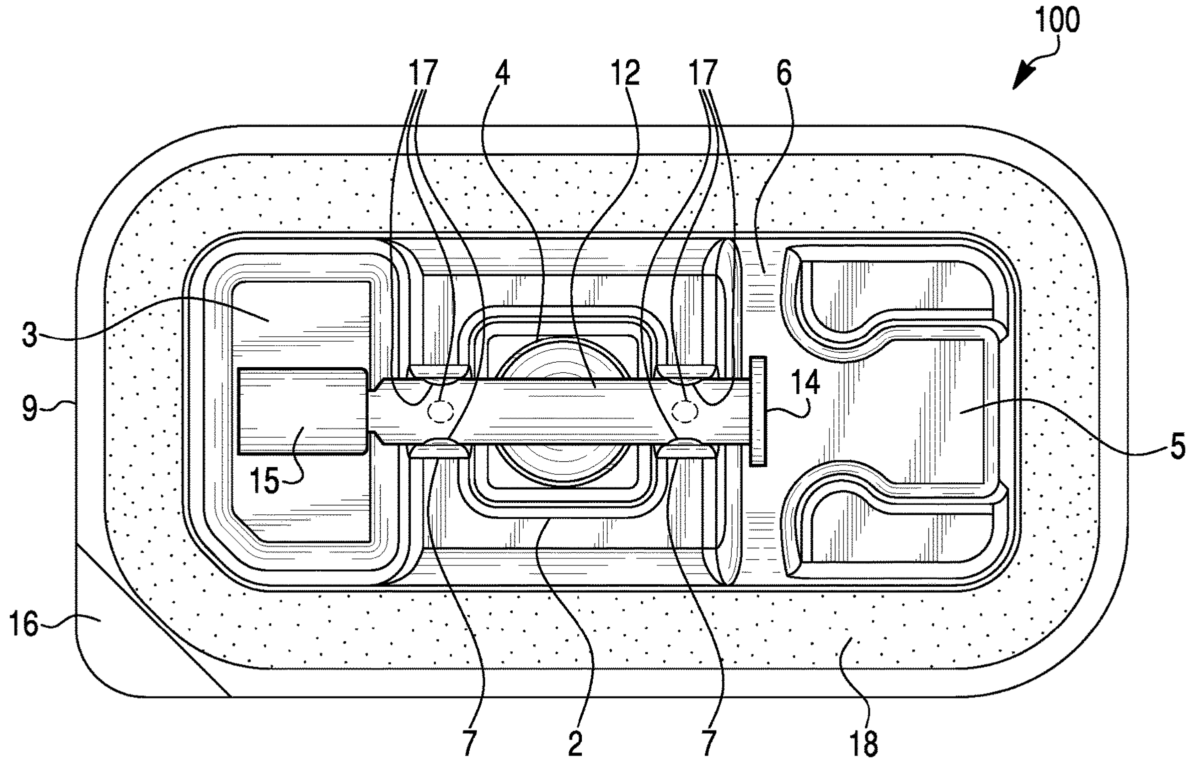
FIG. 4 provides a top view of exemplary packaging, according to an embodiment of the present disclosure.

In some embodiments, pushing dome 4 and/or bending or flexing tray 8 may release the syringe from a friction-fit portion of tray 8. For example, as is shown in FIG. 4, narrowed portions 7 may include one or more geometric features 17 projecting into the narrowed portions to retain the sterile syringe in the cavity via friction fit. Geometric features 17 may be located on the sidewalls of narrowed portions 7 and/or on the bottom of narrowed portions 7 to position syringe barrel 12 within narrowed portions 7. In order to package the syringe within tray 8 so that packaging 100 both facilitates sterilization, e.g., decreases the area of contact with the syringe to make the most surface area of the syringe available for sterilization while still retaining, and suspending the syringe in tray 8 when turned upside down, the syringe may be pushed into tray 8 so that the syringe barrel 12 slides past geometric features 17, allowing the syringe to friction-fit within tray 8. Once syringe barrel 12 is pushed into place in tray 8, geometric features 17 may keep syringe barrel 12 within narrowed portions 7 and may hold the syringe within tray 8. Pushing dome 4 may flex tray 8 and/or may push up syringe barrel 12 so that syringe barrel 12 is moved past geometric features 17, releasing the syringe from tray 8. For example, bending tray 8 may force portions of tray 8 that include geometric features 17 to move away from the syringe and thus to release the syringe. Accordingly, dome 4 may be used in combination with other friction-fit portions of tray 8 to facilitate release of the syringe from tray 8.

One or more geometric features 17 located on the base of narrowed portions 7 may act in conjunction with geometric features 17 on the sidewalls of narrowed portions 7 in order to orient the syringe so that the syringe does not directly touch the sidewalls of narrowed portions 7 and/or of any of the other cavities, e.g., cavities 2, 3, 5 when contained within packaging 100. This may allow a sterilant within packaging 100 to circulate within packaging 100 and around the outer surface of the syringe. By including geometric features 17 to hold the syringe in place while spaced apart from the internal surface of the packaging, geometric features 17 may reduce the surface area of the syringe in contact with the inner walls of packaging 100 and, as a result, may increase the surface area of the syringe that is exposed to a sterilant within packaging 100.

While three geometric features 17 are depicted in each narrowed portion 7 of FIG. 4, it is contemplated that fewer (e.g., two) or more than three geometric features 17 may be included in each narrowed portion 7. Further, geometric features 17 may be included in any suitable portion of tray 8, including any combination of cavities, instead of, or in addition to, narrower portions like narrowed portions 7.

Although reference is made herein to a dome-shaped portion, it should be understood by one of ordinary skill in the art that a projection on tray 8 may have any suitable shape so long as it is capable of being pushed to flex tray 8 and/or to be compressed to an inverted position. Further, although tray 8 is depicted as including three cavities 2, 3, 5, connected to one another by narrowed portions 7, it is contemplated that tray 8 may have any suitable shape with one or more cavities to house a medical device. For example, although embodiments of the present disclosure are drawn to packaging for a syringe, e.g., a pre-filled syringe, it is to be understood that projections, such as dome 4, may be used in conjunction with packaging for any suitable medical device and/or consumer good. Accordingly, tray 8 may be shaped to contain other types of medical devices. Additionally, multiple projections, e.g., multiple domes 4, may be incorporated into tray 8 to facilitate removal of a medical device therein.

As described above, the use of dome 4 in packaging, e.g., blister packaging, to release a syringe housed within the packaging may promote sterility, dose accuracy, and/or safety of the syringe and the user because it may decrease the amount that a user has to directly touch the syringe prior to administration of the syringe contents to a person. This may in turn decrease the risk of accidentally discharging the syringe contents prior to administration of the medicament to a person and reduce the incidence of infection to the person.

Referring back now to FIGS. 1 and 2, packaging 100 may also include a lip 9 extending around at least a portion of tray 8 and defining an opening in tray 8. Lip 9 may allow for a removable, e.g., peelable, cover 28 to be sealed over the top opening of tray 8 to contain the medical device within tray 8 during storage. An adhesive 18, e.g., a glue, paste, film, tape, pressure-sensitive material, and/or cold adhesive, may be used to seal removable cover 28 to lip 9. Adhesive 18 may be compatible for use with the type of external sterilization performed that may be performed on packaging 100. The width of adhesive 18 may be altered depending on the size of the top opening of tray 8, e.g., an increase in size of the top opening of tray 8 will decrease the width of adhesive 18. A corner of lip 9, e.g., corner 16 in FIG. 2, may be free of adhesive 18 to allow a user to lift removable cover 28 off of corner 16 to remove the cover from tray 8. As shown in FIGS. 6 and 8, corner 16 may include a tab 20 (or other projection or indentation) to allow a user to lift removable cover 28 off of corner 16 to remove cover 28 from tray 8. Tab 20 may be included on corner 16 of lip 9 or removable cover 28. In exemplary embodiments, referring to FIGS. 2 and 6, the type, shape and/or size of lip 9 or tab 20 (or other projection or indentation) may be configured to facilitate high speed manufacturing of packaging 100 and/or improve material distribution of packaging 100. Removable cover 28 may be made of any suitable material, e.g., foil paper, plastic, etc., and may be permeable to a suitable gaseous sterilant, such as vaporized hydrogen peroxide or ethyl alcohol.

During use, a user may first remove removable cover 28 from tray 8, e.g., by peeling cover 28 off of lip 9, to expose an opening of tray 8. The user may then orient the opening of tray 8 sideways or up-side-down so that the opening faces a surface onto which the medical device (e.g., pre-filled ophthalmic syringe) is to be ejected. Subsequently or simultaneously, the user may push on dome 4 (or other projection), which may flex tray 8 so that a central portion of the packaging bends towards the medical device while one or more edges of the packaging bend away from the medical device. Pushing dome 4 may cause dome 4 to at least partially invert. In some embodiments, an inverted portion of dome 4 may contact the medical device (e.g., syringe barrel 12), while in other embodiments, dome 4 may never contact the syringe. Pushing dome 4 and flexing tray 8 may thus eject the medical device from tray 8 so that the medical device lands on the surface towards which the opening of tray 8 was oriented. A suitable sterile surface may include, e.g., a sterile table, tray for holding medical devices, cloth, liner, or any other suitable sterile surface. The combination of pushing dome 4, inverting dome 4, bending tray 8, and/or turning tray 8 sideways or up-side-down so that the base of tray 8 is oriented above the syringe and above the sterile surface may allow a user to remove the syringe without actually touching the syringe directly.

In some embodiments, pushing dome 4 and flexing tray 8 may also release the medical device from a friction-fit portion of tray 8, e.g., one or more geometric features 17. Turning tray 8 may allow the syringe to fall out of tray 8 once it is released from tray 8 (e.g., via the inversion of dome 4 and/or bending). In embodiments that include multiple domes 4 (or multiple other projections), multiple domes 4 may be pushed to release the medical device from tray 8 and/or to flex different portions of tray 8.

In the case of packaging for a pre-filled syringe, once the syringe is released from tray 8, any additional packaging on the syringe (e.g., a distal guard or luer lock and/or plunger guard) may be removed from the syringe. In some embodiments, the syringe may be contained in packaging 100 without a needle, and a needle, e.g., a stake needle, may be attached to a distal end of the syringe, e.g., via a needle attachment. The contents of the syringe (e.g., large molecule and/or small molecule antagonists of VEGF and/or ANG-2, such as aflibercept (Eylea®), ranibizumab (Lucentis®), bevacizumab (Avastin®), conbercept, OPT-302, RTH258 (brolucizumab), a pegylated designed ankyrin repeating protein (DARPin) like abicipar pegol, or RG7716) may then be injected into an eye of a recipient.

Figure 9:
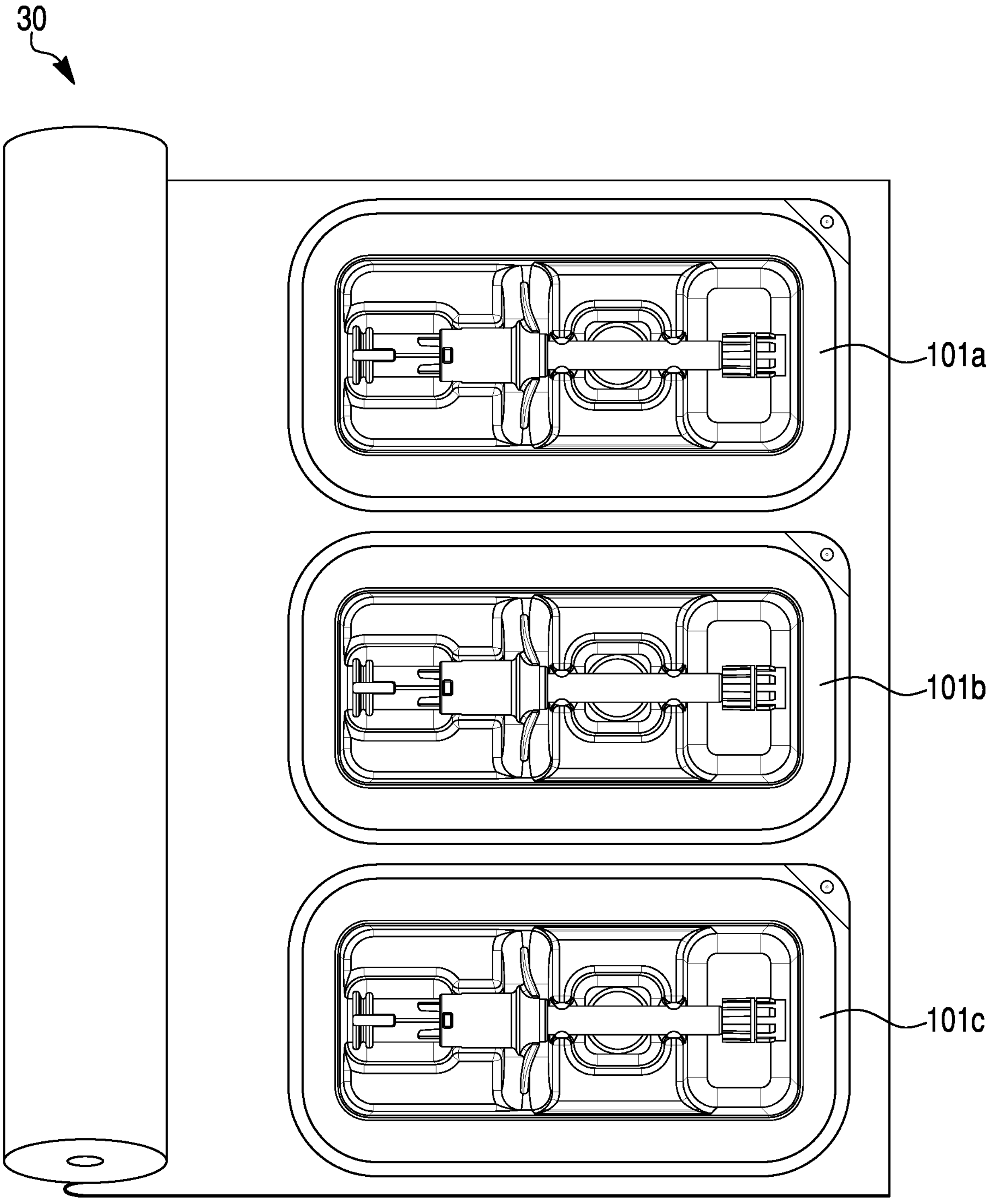
FIG. 9 provides a bottom view of exemplary packaging containing syringes that are printed according to an embodiment of the present disclosure.

As described above, components of packaging 100, and the size and/or shape of such components may be configured to facilitate high speed manufacturing of packaging 100 and/or improve material distribution of packaging 100. FIG. 9 is an exemplary embodiment showing a portion of the manufacturing process of packaging 100, where for example, packaging 101*a*, 101*b*, and 101*c*, are sealed with material 30 to form removable cover 28 (FIG. 3), which may be, e.g., Tyvek or other suitable high-density polyethylene fibers, ethylene-vinyl acetate, and/or other thermoplastic materials.

The description above and examples are illustrative, and are not intended to be restrictive. One of ordinary skill in the art may make numerous modifications and/or changes without departing from the general scope of the invention. For example, and as has been referenced, the above-described embodiments (and/or aspects thereof) may be used in combination with each other. Additionally, portions of the above-described embodiments may be removed without departing from the scope of the invention. In addition, modifications may be made to adapt a particular situation or aspect to the teachings of the various embodiments without departing from their scope. Many other embodiments will also be apparent to those of skill in the art upon reviewing the above description.

What is claimed is:

1. A method of removing a syringe from a packaging, the method comprising:

peeling off a removable cover from a blister packaging tray of the packaging, the blister packaging tray having a cavity configured to contain the syringe therein, wherein the blister packaging tray includes a dome-shaped projection associated with and extending away from a base of the cavity of the blister packaging tray in a direction opposite to an opening of the cavity, and the dome-shaped projection is aligned with the syringe;

pushing a portion of the dome-shaped projection towards the cavity of the blister packaging tray, wherein pushing the portion of the dome-shaped projection causes a portion of the blister packaging tray to flex; and orienting the blister packaging tray so that the opening of the cavity faces a sterile surface to release the syringe from the blister packaging tray.

2. The method of claim 1, wherein the syringe is pre-filled with aflibercept, ranibizumab, bevacizumab, conbercept, OPT-302, RTH258 (brolucizumab), a pegylated designed ankyrin repeating protein (DARPin), or RG7716.

3. The method of claim 1, wherein the blister packaging tray is fabricated from a material including one or more of polypropylene, polystyrene, polyethylene, polycarbonate, polyvinyl chloride, or polyethylene terephthalate glycol.

4. The method of claim 1, wherein the removable cover is permeable to a gaseous sterilant.

5. The method of claim 4, wherein the gaseous sterilant is vaporized hydrogen peroxide.

6. The method of claim 1, wherein the syringe includes a barrel with an outer diameter and the dome-shaped projection includes a diameter greater than the outer diameter of the barrel.

7. A method of removing a syringe from a packaging, the packaging including a tray having a cavity, a dome-shaped projection associated with the cavity, and an opening covered by a gas-permeable material, wherein the dome-shaped projection extends away from a base of the cavity in a direction opposite to the opening of the tray;

the method comprising:

removing the gas-permeable material so as to expose the opening of the tray;

pushing the dome-shaped projection towards the cavity and a barrel of the syringe, wherein the step of pushing the dome-shaped projection also causes a portion of the tray to flex; and ejecting the syringe from the tray.

8. The method of claim 7, wherein ejecting the syringe from the tray is performed without a user directly handling the syringe.

9. The method of claim 7, wherein the gas-permeable material is permeable to vaporized hydrogen peroxide or ethylene oxide.

10. The method of claim 7, wherein the dome-shaped projection includes a bulbous shape and a diameter that is greater than an outer diameter of the barrel of the syringe.

11. The method of claim 10, wherein the diameter of the dome-shaped projection defines a widest portion of the bulbous shape where the dome-shaped projection meets the base of the cavity.

12. The method of claim 7, wherein the syringe is pre-filled with aflibercept, ranibizumab, bevacizumab, ranibizumab, bevacizumab, conbercept, OPT-302, RTH258 (brolucizumab), a pegylated designed ankyrin repeating protein (DARPin), or RG7716.

13. The method of claim 7, wherein, prior to the removing step, the packaging containing the syringe is sterilized with a gaseous sterilant.

14. The method of claim 7, wherein the gas-permeable material is formed of one or more of high-density polyethylene fibers, ethylene-vinyl acetate, or thermoplastic materials.

15. The method of claim 7, wherein the dome-shaped projection includes a dome having a widest diameter at the base of the cavity, wherein the dome-shaped projection extends directly outward from the base such that the widest diameter of the dome is connected at the base.

16. The method of claim 15, wherein when the syringe is disposed within the cavity, a height of the dome-shaped projection from an apex of the dome to a base of the dome-shaped projection is greater than a distance between the base of the dome-shaped projection and a portion of the syringe contained within the cavity and overlying the dome-shaped projection.

17. The method of claim 7, wherein the dome-shaped projection is hollow and open towards the cavity.

18. A method of removing a syringe from a packaging that includes a flexible tray having a base for receiving the syringe and a dome-shaped projection extending away from the base in a direction opposite to the syringe;

the method comprising:

removing a cover that is coupled to the flexible tray and disposed over the base to expose an opening of the flexible tray, wherein the cover is permeable to a gaseous sterilant;

pushing the dome-shaped projection towards the syringe to flex a portion of the base, wherein the dome-shaped projection is hollow and open towards the opening of the flexible tray; and ejecting the syringe from the base.

19. The method of claim 18, wherein the dome-shaped projection is configurable to move relative to the base in response to receiving a force at a portion of the dome-shaped projection when pushing the dome-shaped projection.

20. The method of claim 18, wherein the base defines a cavity that includes a first cavity portion configured to contain a plunger of the syringe, a second cavity portion configured to contain a barrel of the syringe, and a third cavity portion configured to contain a needle attachment portion of the syringe; and wherein the dome-shaped projection extends away from the second cavity portion.

* * * * *